US006991782B2

(12) United States Patent
Kanji et al.

(10) Patent No.: US 6,991,782 B2
(45) Date of Patent: Jan. 31, 2006

(54) COSMETIC COMPOSITIONS COMPRISING AT LEAST ONE POLYMETHYLSILSESQUIOXANE FILM FORMER

(75) Inventors: Mohamed Kanji, Edison, NJ (US); Carl Orr, Scotch Plains, NJ (US); Valerie Robert, Chevilly Larue (FR)

(73) Assignee: L'Oréal, Paris (FR)

( * ) Notice: Subject to any disclaimer, the term of this patent is extended or adjusted under 35 U.S.C. 154(b) by 0 days.

(21) Appl. No.: 09/883,229

(22) Filed: Jun. 19, 2001

(65) Prior Publication Data

US 2002/0031488 A1 Mar. 14, 2002

Related U.S. Application Data

(60) Provisional application No. 60/212,640, filed on Jun. 19, 2000.

(51) Int. Cl.
*A61K 7/02* (2006.01)
(52) U.S. Cl. .................. 424/70.7; 424/70.12; 424/401
(58) Field of Classification Search .................. 424/63, 424/64, 70.7, 70.121, 401, 70.1; 514/937, 514/938
See application file for complete search history.

(56) References Cited

U.S. PATENT DOCUMENTS

| | | | |
|---|---|---|---|
| 2,465,188 A | 3/1949 | Barry et al. | |
| 4,892,726 A | 1/1990 | Yonekura et al. | |
| 5,047,492 A | 9/1991 | Weidner et al. | |
| 5,085,859 A * | 2/1992 | Halloran et al. | 424/70.121 |
| 5,246,694 A | 9/1993 | Birthwistle | |
| 5,439,673 A | 8/1995 | Murray | |
| 5,654,362 A | 8/1997 | Schultz, Jr. et al. | |
| 5,676,938 A | 10/1997 | Kimura et al. | |
| 5,756,082 A | 5/1998 | Cashin et al. | |
| 5,800,816 A | 9/1998 | Brieva et al. | |
| 5,911,974 A | 6/1999 | Brieva et al. | |
| 5,959,009 A | 9/1999 | Konik et al. | |
| 5,965,112 A | 10/1999 | Brieva et al. | |
| 6,019,962 A | 2/2000 | Rabe et al. | |
| 6,045,782 A * | 4/2000 | Krog et al. | 424/401 |
| 6,071,503 A | 6/2000 | Drechsler et al. | |
| 6,074,654 A | 6/2000 | Drechsler et al. | |
| 6,423,306 B2 * | 7/2002 | Caes et al. | 424/401 |

FOREIGN PATENT DOCUMENTS

| | | |
|---|---|---|
| CA | 2123549 | 11/1994 |
| EP | 0 295 886 B1 | 1/1992 |
| EP | 0 497 144 B1 | 8/1992 |
| EP | 0 560 879 B1 | 9/1993 |
| GB | 2 188 655 A | 10/1987 |
| JP | A-61-018708 | 1/1986 |
| JP | A-61-065808 | 4/1986 |
| JP | A-61-065809 | 4/1986 |
| JP | A-61-158910 | 7/1986 |
| JP | A-61-158913 | 7/1986 |
| JP | A-61-158914 | 7/1986 |
| JP | A-61-161209 | 7/1986 |
| JP | A-61-161211 | 7/1986 |
| JP | A-61-195009 | 8/1986 |
| JP | A-62-234012 | 10/1987 |
| JP | A6-62-298519 | 12/1987 |
| JP | A-62-298511 | 12/1987 |
| JP | A-62-298512 | 12/1987 |
| JP | A-62-298518 | 12/1987 |
| JP | A-63-022010 | 1/1988 |
| JP | A-63-313710 | 12/1988 |
| JP | A-63-313713 | 12/1988 |
| JP | A-02-42008 | 2/1990 |
| JP | A-63-297313 | 5/1998 |
| WO | WO 98/38981 | 9/1998 |
| WO | WO 98/42298 | 10/1998 |

OTHER PUBLICATIONS

JP Abstract 5025019 A (Jul. 1991).*
Commerical Product Label—Revlon Colorstay® (1 page).
English language DERWENT Abstract of JP-A-61-018708.
English language DERWENT Abstract of JP-A-61-065808.
English language DERWENT Abstract of JP-A-61-065809.
English language DERWENT Abstract of JP-A-61-158910.
English language DERWENT Abstract of JP-A-61-158913.
English language DERWENT Abstract of JP-A-61-158914.
English language DERWENT Abstract of JP-A-61-161209.
English language DERWENT Abstract of JP-A-61-161211.
English language DERWENT Abstract of JP-A-61-195009.
English language DERWENT Abstract of JP-A-62-234012.
English language DERWENT Abstract of JP-A-62-298511.
English language DERWENT Abstract of JP-A-62-298512.
English language DERWENT Abstract of JP-A-62-298518.
English language DERWENT Abstract of JP-A-62-298519.
English language DERWENT Abstract of JP-A-63-022010.
English language DERWENT Abstract of JP-A-63-297313.
English language DERWENT Abstract of JP-A-63-313710.
English language DERWENT Abstract of JP-A-63-313713.
English language DERWENT Abstract of JP-A-02-42008.

* cited by examiner

*Primary Examiner*—Jyothsna Venkat
(74) *Attorney, Agent, or Firm*—Finnegan, Henderson, Farabow, Garrett and Dunner LLP

(57) ABSTRACT

Compositions comprising at least one polymethylsilsesquioxane film former and at least one film former different from said at least one polymethylsilsesquioxane film former, wherein said at least one polymethylsilsesquioxane film former is present in an amount effective to provide at least one property chosen from long wear and transfer resistance.

33 Claims, No Drawings

COSMETIC COMPOSITIONS COMPRISING AT LEAST ONE POLYMETHYLSILSESQUIOXANE FILM FORMER

This application is a non-provisional application based on U.S. provisional application No. 60/212,640, filed Jun. 19, 2000, the disclosure of which is incorporated herein by reference.

The present invention provides compositions comprising at least one polymethylsilsesquioxane film former and at least one film former different from the at least one polymethylsilsesquioxane film former. The inventive compositions may impart at least one property chosen from transfer resistance, long wear, and waterproof properties to cosmetic, dermatological and/or pharmaceutical products.

Many compositions, including pigmented cosmetic compositions (such as foundations, mascaras, lip compositions, eyeliners), other cosmetic compositions, and sunscreen compositions, attempt to provide longer wear and transfer resistance. Compositions which form a film after application may exhibit such properties. Generally, film forming compositions contain volatile solvents which evaporate on contact with the skin or other keratinous material, and leave behind a layer comprising waxes and/or resins, and any pigments, fillers and active agents. Formation of a suitable film may require the liquid or carrier (solvent) to evaporate at a rate that allows a film to form continuously and to be free from imperfections.

Different types of polymers have been used in an attempt to achieve such film formation. One such type of polymer is silicone resins. Silicone resin nomenclature is known in the art as "MDTQ" nomenclature, whereby a silicone resin is described according to the various monomeric siloxane units which make up the polymer.

Each letter of "MDTQ" denotes a different type of unit. The letter M denotes the monofunctional unit $(CH_3)_3SiO_{1/2}$. This unit is considered to be monofunctional because the silicone atom only shares one oxygen when the unit is part of a polymer. The "M" unit can be represented by the following structure:

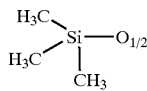

At least one of the methyl groups of the M unit may be replaced by another group, e.g., to give a unit with formula $[R(CH_3)_2]SiO_{1/2}$, as represented in the following structure:

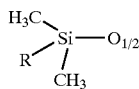

wherein R is chosen from groups other than methyl groups. Non-limiting examples of such groups other than methyl groups include alkyl groups other than methyl groups, alkene groups, alkyne groups, hydroxyl groups, thiol groups, ester groups, acid groups, ether groups, wherein the groups other than methyl groups may be further substituted.

The symbol D denotes the difunctional unit $(CH_3)_2SiO_{2/2}$ wherein two oxygen atoms bonded to the silicone atom are used for binding to the rest of the polymer. The "D" unit, which is the major building block of dimethicone oils, can be represented as:

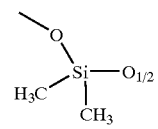

The symbol T denotes the trifunctional unit, $(CH_3)SiO_{3/2}$ and can be represented as:

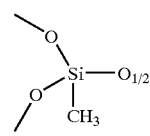

Similarly, the symbol Q denotes the tetrafunctional unit, $SiO_{4/2}$ wherein all four oxygens bonded to the silicone atom are bonded to the rest of the polymer.

Thus, a vast number of different silicone polymers can be manufactured. Further, it would be clear to one skilled in the art that the properties of each of the potential silicone polymers will vary depending on the type(s) of monomer(s), the type(s) of substitution(s), the size of the polymeric chain, the degree of cross linking, and size of any side chain(s). For example, different properties will be observed depending on whether the backbone is a silicone chain with carbon-based side chains or is carbon-based with silicone side chains.

Non-limiting examples of silicone polymers which may be useful in cosmetic compositions include silanes, siloxanes, siloxysilicates, and silsesquioxanes. A non-limiting example of such a siloxane is polydimethylsiloxane (PDMS). Polydimethylsiloxanes are generally composed of long straight chains of $(CH_3)_2SiO_{2/2}$ (i.e., D units) and have viscosities which are dependent on both the size of the polymer and the presence and nature of any substituent(s) on the polymer. A non-limiting example of a siloxysilicate is trimethylsiloxysilicate, which may be represented by the following formula:

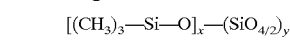

(i.e, MQ units) wherein x and y may, for example, range from 50 to 80. Silsesquioxanes, on the other hand, may be represented by the following formula:

(i.e., T Units) wherein x may, for example, have a value of up to several thousand.

Polymethylsilsesquioxanes are silsesquioxanes that do not have a substituent replacing the methyl groups. Certain polymethylsilsesquioxanes have previously been used in hair care compositions. See, e.g., U.S. Pat. No. 5,246,694, the disclosure of which is incorporated herein by reference, which discloses a shampoo composition comprising a surfactant, an aqueous emulsion of highly viscous silicone in volatile silicone and a cationic polymer which is a derivative of guar gum. The highly viscous silicone disclosed therein may be chosen from silicone resins including a polymethylsilsesquioxane such as Resin MK (also called SiliconHarz MK) which is available from Wacker, and a siloxysilicate such as Resin MQ which is available from General Electric and Dow Corning.

The Resin MK and Resin MQ silicone resins may form a film after the volatile carrier has evaporated. The MQ film is generally hard and brittle at room temperature, while the MK film is generally continuous and flexible, i.e., not brittle. Depending on the application, plasticizers may be added to help obtain a more flexible, thus more comfortable, film.

Similarly, U.S. Pat. No. 5,439,673, the disclosure of which is incorporated herein by reference, discloses the use of silicone resins in a hair care composition. The resins disclosed therein again include Resin MK and Resin MQ. Further, EP 0 560 879 B1, the disclosure of which is incorporated herein by reference, discloses the use of similar resins (MQ, MT, MTQ, and MDTQ resins) in hair conditioning compositions.

The use of certain silicone polymers or derivatives thereof as film formers in cosmetic compositions has also been disclosed. See e.g., U.S. Pat. Nos. 5,965,112; 5,800,816; 5,911,974; and 5,959,009, the disclosures of which are incorporated herein by reference. However, these compositions may be uncomfortable to wear as the composition that remains on the skin or other keratinous material may be a brittle or non-flexible film. These compositions may also tend to flake off the skin or other keratinous material due to poor adhesion to the material. Furthermore, prior to application, these compositions may be tacky, which may result in poor application and spreadability characteristics.

There is, therefore, a need for improved long wearing cosmetic compositions which limit transfer to other materials such as, for example, skin or fabric, i.e., transfer resistant compositions, which also possess good cosmetic properties such as, for example, wearing comfort and waterproof properties, and which are not tacky or "draggy" during and after application.

The present invention is directed to compositions which may overcome at least one of the aforementioned disadvantages and which may make it possible to obtain a film having at least one property chosen from long wear, transfer resistance and waterproof properties. The compositions may also provide at least one additional property chosen from flexibility, wearability, good drying time, good retention, lack of tackiness, and low migration over time.

Thus, in one aspect, the present invention relates to compositions comprising at least one polymethylsilsesquioxane film former and at least one film former which is different from the at least one polymethylsilsesquioxane film former, wherein the at least one polymethylsilsesquioxane film former is present in an amount effective to provide at least one property chosen from long wear and transfer resistance. In one embodiment, the at least one polymethylsilsesquioxane film former is present in the inventive composition in an amount effective to provide both long wear and transfer resistance.

In another aspect, the present invention relates to an emulsion comprising at least one polymethylsilsesquioxane film former and at least one film former different from the at least one polymethylsilsesquioxane film former, wherein the emulsion is in the form of a water-in-oil emulsion or an oil-in-water emulsion, and further wherein the at least one polymethylsilsesquioxane film former is present in an amount effective to provide at least one property chosen from long wear and transfer resistance. In one embodiment, the at least one polymethylsilsesquioxane film former is present in the inventive composition in an amount effective to provide both long wear and transfer resistant properties.

Further, the present invention provides cosmetic foundation compositions, mascara compositions, sunscreen compositions, eyeliner compositions, and make-up compositions for lips, wherein each of the compositions comprises at least one polymethylsilsesquioxane film former and at least one film former which is different from the at least one polymethylsilsesquioxane film former, wherein the at least one polymethylsilsesquioxane film former is present in an amount effective to provide at least one property chosen from long wear and transfer resistance. In certain embodiments, the at least one polymethylsilsesquioxane film former is present in the inventive composition in an amount effective to provide both long wear and transfer resistance.

Certain terms used herein are defined below:

"At least one" as used herein means one or more and thus includes individual components as well as mixtures/combinations.

"Film former" as used herein means a polymer that, after dissolution in at least one solvent (such as, for example, water and organic solvents), leaves a film on the substrate to which it is applied once the at least one solvent evaporates.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human lips followed by "kissing" a material, for example, a sheet of paper, after expiration of a certain amount of time following application, such as 2 minutes after application. Similarly, transfer resistance of a composition may be evaluated by the amount of product transferred from a wearer to any other substrate, such as transfer from the neck of an individual to a collar after the expiration of a certain amount of time following application. The amount of composition transferred to the substrate (e.g., collar, or paper) may then be evaluated and compared. For example, a composition may be transfer resistant if a majority of the product is left on the wearer, e.g., lips, neck, etc. In one embodiment, little or no composition is transferred to the substrate. Further, the amount transferred may be compared with that transferred by other compositions, such as commercially available compositions.

"Long wear" compositions as used herein, refers to compositions where at least one property chosen from consistency, texture, and color remains the same as at the time of application, as viewed by the naked eye, after an extended period of time, such as, for example, 1 hour, 2 hours, and further such as 8 hours. Long wear properties may be evaluated by any method known in the art for evaluating such properties. For example, long wear may be evaluated by a test involving the application of a composition to human skin (including lips) and evaluating the consistency, texture and color of the composition after an extended period of time. For example, the consistency, texture and color of a lip composition may be evaluated immediately following application and these characteristics may then be re-evaluated and compared after an individual has worn the lip composition for a certain amount of time. Further, these characteristics may be evaluated with respect to other compositions, such as commercially available compositions.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In one embodiment, little or no composition is transferred from the wearer.

A "pigment" as used herein includes white inorganic particles, colored inorganic particles, white organic particles, and colored organic particles.

"Fillers" as used herein includes lamellar inorganic particles, nonlamellar inorganic particles, lamellar organic particles, nonlamellar organic particles, lamellar, wherein the particles may be colorless or white.

"Mothers-of pearl" as used herein refers to irridescent particles, such as those produced by certain mollusks in their shell, and synthetic irridescent particles.

"Polymers" as defined herein comprise copolymers (including terpolymers) and homopolymers.

A "di-block copolymer" as defined herein is an A-B type copolymer wherein the copolymer comprises, for example, a hard segment (A) bonded to a soft segment (B) in sequence.

A "tri-block copolymer" as defined herein is an A-B-A type copolymer wherein the copolymer comprises, for example, one hard segment bonded to one soft segment which, in turn, is bonded to another hard segment.

"Multiblock copolymers," "radial copolymers" and "star copolymers" as used herein comprise those copolymers that comprise a combination of both hard and soft segments, provided that there are both hard and soft characteristics It is to be understood that both the foregoing general description and the following detailed description are exemplary and explanatory only and are not restrictive of the invention, as claimed. Reference will now be made in detail to exemplary embodiments of the present invention.

The compositions of the present invention comprise at least one polymethylsilsesquioxane film former, that is, a film forming silsesquioxane that does not have a substituent replacing the methyl groups of the T units. The at least one polymethylsilsesquioxane film former of the present invention is necessarily a film former. Not all polymethylsilsesquioxanes are film formers, and thus, not all polymethylsilsesquioxanes are encompassed within the scope of the present invention. For example, the highly polymerized polymethylsilsesquioxanes (T Resins), such as Tospearl™ from Toshiba and KMP590 from Shin-Etsu, are highly insoluble and therefore are not film formers according to the present invention. The molecular weights of the aforementioned polymethylsilsesquioxanes are difficult to determine, and they generally contain at least 1000 T units.

According to one embodiment of the present invention, the number of T units of the at least one polymethylsilsesquioxane film former is less than or equal to 500. In another embodiment, the number of T units of the at least one polymethylsilsesquioxane film former ranges from 50 to 500. In yet another embodiment, the at least one polymethylsilsesquioxane film former has a melting point ranging from 40° C. to 80° C. Further, the at least one polymethylsilsesquioxane film former according to the present invention is soluble in solvents chosen from volatile silicones and organic solvents. The weight-average molecular weight of the at least one polymethylsilsesquioxane film former generally ranges from 500 to 50,000, such as from 500 to 20,000, and further such as a weight average molecular weight of 10,000.

A non-limiting example of the at least one polymethylsilsesquioxane film former is Belsil PMS MK, also referred to as Resin MK, available from Wacker Chemie. This polymethylsilsesquioxane film former is a polymer comprising polymerized repeating units of $CH_3SiO_{3/2}$ (T units) and may also contain up to 1% by weight or by mole of units of the formula $(CH_3)_2SiO_{2/2}$ (D units). The weight-average molecular weight of this polymer has been estimated to be 10,000. It is believed that the polymers are in a "cage" and "ladder" configuration, as exemplified in the figures below. The weight-average molecular weight of the "cage" unit has been calculated to be 536 g/mol. The majority of the polymer is in the "ladder" configuration, wherein the ends of the polymer are capped with ethoxy ($CH_3CH_2O$) groups. The ethoxy groups are generally present in an amount of 4.5% by weight and the mole percent is generally 7% (silicone units). As ethoxy groups may react with water, a small and variable amount of SiOH may also be present in the polymer.

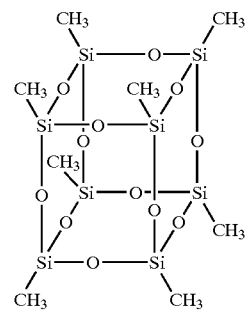

Cage

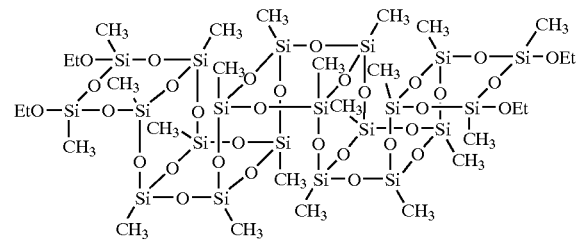

Ladder

Another non-limiting example of the at least one polymethylsilsesquioxane film former suitable for use in the present invention is KR-220L, which is available from SHIN-ETSU. This polymethylsilsesquioxane film former is composed of silicone T-units (i.e, those of formula $CH_3SiO_{3/2}$) and has Si—OH (or silanol) end units. There are no D units in KR-220L.

Other non-limiting examples of the at least one polymethylsilsesquioxane film former that may be useful in the practice of the invention include KR-242A (which is comprised of methyl T units (98%) and dimethyl D units (2%) and has Si—OH end units) and KR-251 (which is comprised of methyl T units (88%) and dimethyl D units (12%) and has Si—OH end units), both of which are available from SHIN-ETSU.

Depending on the application, the concentration of the at least one polymethylsilsesquioxane film former in the presently claimed composition may vary considerably. One of skill in the art will be able to determine routinely the amount of the at least one polymethylsilsesquioxane film former depending on the desired application.

For example, for cosmetic foundations, the at least one polymethylsilsesquioxane film former may be present in the composition in an amount generally ranging from 0.1% to 30% by weight relative to the total weight of the composition, such as from 1% to 15% by weight. For eyeliner compositions, the at least one polymethylsilsesquioxane film former may be present in an amount generally ranging from 5% to 70% by weight relative to the total weight of the composition, such as from 20% to 70% by weight. For lip compositions, such as lipstick, the at least one polymethylsilsesquioxane film former may be present in an amount generally ranging from 1% to 70% by weight relative to the total weight of the composition, such as from 10% to 70% by weight. For mascara compositions, the at least one polymethylsilsesquioxane film former may be present in an amount generally ranging from 1% to 25% by weight relative to the total weight of the composition, such as from 5% to 20% by weight. In one embodiment, the at least one polymethylsilsesquioxane film former is present in the composition in a higher amount than the at least one film former different from the at least one polymethylsilsesquioxane film former. One of ordinary skill in the art will recognize that the at least one polymethylsilsesquioxane film former different from the at least one polymethylsilsesquioxane film former according to the present invention may be commercially available, and may come from suppliers in the form of a dilute solution. The amounts of the at least one polymethylsilsesquioxane film former disclosed herein therefore reflect the weight percent of active material.

Thus, as the inventive compositions may be used in a variety of cosmetic, dermatological and/or pharmaceutical products, the effective amount of the at least one polymethylsilsesquioxane film former in a product (whether cosmetic or dermatological or pharmaceutical) is the amount necessary to obtain the desired degree of at least one property chosen from long wear and transfer resistance. One of ordinary skill in the art will also be able to determine routinely the amount of the at least one polymethylsilsesquioxane film former, the at least one film former different from the at least one polymethylsilsesquioxane film former, and any other ingredients, if present, needed to obtain a stable product depending on the application.

According to the present invention, the at least one film former different from the at least one polymethylsilsesquioxane film former may, for example, be chosen from those listed at pages 1744 to 1747 of the CTFA International Cosmetic Ingredient Dictionary, 8$^{th}$ edition (2000). In one embodiment, the at least one film former different from the at least one polymethylsilsesquioxane film former is chosen from di-block copolymer film formers, tri-block copolymer film formers, multi-block copolymer film formers, radial copolymer film formers, and star block copolymer film formers, wherein the at least one film former different from the at least one polymethylsilsesquioxane film former comprises at least two thermodynamically incompatible segments. As defined herein, the foregoing copolymers comprise distinctive arrangements of both hard and soft segments. A non-limiting example of a hard segment is styrene, while non-limiting examples of soft segments include ethylene, propylene, butylene and combinations of any of the foregoing soft segments.

Non-limiting examples of the at least one film former different from the at least one polymethylsilsesquioxane film former useful in the present invention include: vinylpyrrolidone/vinyl acetate (PVP/VA) copolymers, such as Luviskol® VA copolymers available from BASF® Corporation and PVP/VA series copolymers available from from ISP; acrylic fluorinated emulsion film formers, such as Foraperle® film formers (e.g., Foraperle® 303 D available from Elf Atochem), although Foraperle® may not be suitable for some cosmetic formulations; GANEX® copolymers, such as butylated PVP, PVP/Hexadecene copolymers, PVP/Eicosene copolymers, and tricontanyl; Poly(vinylpyrrolidone/diethylaminoethyl methacrylate) copolymers and PVP/Dimethylaminoethylmethacrylate copolymers such as Copolymer 845 available from I.S.P.; Resin ACO-5014 (Imidized IB/MA copolymer); other PVP based polymers and copolymers; silicone gums; cyclomethicone copolymers and dimethicone crosspolymers, such as Dow Corning® 2-9040 and those disclosed in U.S. Pat. No. 5,654,362, the disclosure of which is hereby incorporated by reference; trimethyl siloxysilicates such as SR 1000, 554230, and SS4267 available from GE Silicones; alkyl cycloalkylacrylate copolymers, such as those disclosed in WO 98/42298, the disclosure of which is hereby incorporated by reference; Mexomere® film formers and other allyl stearate/vinyl acetate copolymers; polyolprepolymers, such as PPG-12/SMDI copolymer, also called Poly(oxy-1,2-ethanediyl), α-hydro-ω-hydroxy-polymer with 1,1'-methylene-bis-(4-isocyanatocyclohexane) available from Barnet; and Avalure™ AC Polymers (Acrylates Copolymer) and Avalure™ UR polymers (Polyurethane Dispersions), available from BFGoodrich.

In one embodiment, the at least one film former different from the at least one polymethylsilsesquioxane film former is chosen from Kraton® rubber copolymers (which are available from Shell Chemical Company) and similar gelling agents. The Kraton® rubber configuration is well known in the art and any block copolymer film former, such as gelling agents, with a similar configuration is within the practice of the invention. In another embodiment, the at least one film former different from the at least one polymethylsilsesquioxane film former is chosen from Kraton® rubber copolymers and is present in a gel in an amount ranging from 10% to 20% by weight relative to the total weight of the composition.

Each molecule of Kraton® rubber comprises block segments of (i) styrene units and (ii) rubber monomer and/or co-monomer units. Thus, Kraton® rubber copolymers are thermoplastic elastomers in which the polymer chains have a configuration chosen from tri-block configurations, di-block configurations, radial block configurations, star block configurations and mixtures of any of the foregoing configurations. The configurations of each of the Kraton® rubbers form separate polystyrene and rubber domains.

The Kraton® tri-block rubber copolymers are comprised of polystyrene segments on each end of a rubber segment, while the Kraton® di-block rubber copolymers are comprised of a polystyrene segment attached to a rubber segment. The most common Kraton® triblock copolymers are linear A-B-A block type styrene-butadiene-styrene copolymers, linear A-B-A block styrene-isoprene-styrene copolymers, and linear A-B-A block styrene-ethylenebutylene-styrene copolymers. Non-limiting examples of the Kraton® di-block copolymers include AB block type copolymers such as styrene-ethylenepropylene copolymers, styrene-ethylenebutylene copolymers, styrene-butadiene copolymers, and styrene-isoprene copolymers. The Kraton® radial or star configuration, in another embodiment, may, for example, be a four-point or other multipoint star made of rubber with a polystyrene segment attached to each end of a rubber segment.

In another embodiment, the at least one film former different from the at least one polymethylsilsesquioxane film former is chosen from block copolymer film formers comprising at least one styrene/butylene/ethylene/styrene copolymer (tri-block) and at least one ethylene/propylene/styrene copolymer (radial or star block). Similarly, corresponding block copolymers which are referred to as "hydrogenated" block copolymers by the manufacturer (e.g., hydrogenated styrene/butylene/ethylene/styrene copolymer (tri-block) and hydrogenated ethylene/propylene/styrene copolymer (radial or star block)) are within the scope of the invention. Non-limiting examples of suitable block copolymer film formers include Versagel M5960 and Versagel M5970, which are available from Penreco of Houston Tex., and block copolymers available from Brooks Industries, such as Gel Base.

According to the present invention, the at least one film former different from the at least one polymethylsilsesquioxane film former may be formulated by dissolving it in at least one solvent. In one embodiment, the at least one solvent is chosen from hydrocarbons. Non-limiting examples of hydrocarbons useful in the practice of the invention include mineral oils, mineral solvents, mineral spirits, petroleum, waxes, synthetic hydrocarbons, animal oils, vegetable oils. For example, the at least one film former different from the at least one polymethylsilsesquioxane film former may be formulated by dissolving it in isododecane and/or a light paraffinic solvent. In another embodiment, the at least one solvent is chosen from non-hydrocarbon solvents. Non-limiting examples of non-hydrocarbon solvents include amyl acetate, butyl acetate, isobutyl acetate, ethyl acetate, propyl acetate, and isopropyl acetate.

The solvent and solubility conditions for formulating the at least one film former different from the at least one polymethylsilsesquioxane film former will be chosen by a person skilled in the art in order to prepare a composition which has the desired properties. One of ordinary skill in the art will be able to determine the solubility parameters and choose a solvent based on the at least one film former different from the at least one polymethylsilsesquioxane film former chosen for the envisaged application. More information regarding solubility parameters and solvents useful in the processing of specific film formers is available from the various manufacturers, e.g., Shell Chemical Company. Additional discussions of polymer solubility parameter concepts are presented in: Encyclopedia of Polymer Science and Technology, Vol. 3, Interscience, New York (1965) and Encyclopedia of Chemical Technology, Supp. Vol., Interscience, New York (1971), the disclosures of which are hereby incorporated by reference.

In one embodiment, the at least one film former different from the at least one polymethylsilsesquioxane film former according to the present invention is water insoluble, can be processed at room temperature, offers excellent adherence to the skin, and is tack free. In another embodiment, the at least one film former different from the at least one polymethylsilsesquioxane film former is present in the continuous phase of a cosmetic formulation in a high concentration. In yet another embodiment, the at least one film former different from the at least one polymethylsilsesquioxane film former is compatible with other components which may be comprised within the same phase.

According to the present invention, the amount of the at least one film former different from the at least one polymethylsilsesquioxane film former may readily be determined by one of skill in the art and can vary considerably depending on the desired application. For example, for cosmetic compositions, the at least one film former different from the at least one polymethylsilsesquioxane film former may be present in the cosmetic composition in an amount generally ranging from 1% to 55% by weight relative to the total weight of the composition, such as from 1% to 25% by weight. One of ordinary skill in the art will recognize that the at least one film former different from the at least one polymethylsilsesquioxane film former former according to the present invention may be commercially available, and may come from suppliers in the form of a dilute solution. The amounts of the at least one film former different from the at least one polymethylsilsesquioxane film former disclosed herein therefore reflect the weight percent of active material.

In one embodiment, the inventive composition is an emulsion, such as a water-in-oil emulsion or an oil-in-water emulsion. While the at least one polymethylsilsesquioxane and the at least one film former different from the at least one polymethylsilsesquioxane film former of the present invention may be in the water or in the oil phase of an emulsion, in certain embodiments, maximum efficacy has been demonstrated when the at least one polymethylsilsesquioxane and the at least one film former different from the at least one polymethylsilsesquioxane film former are in the oil phase.

The inventive compositions of the present invention may further comprise at least one additional ingredient different from both the at least one polymethylsilsesquioxane film former and the at least one film former different from the at least one polymethylsilsesquioxane film former of the present invention. Non-limiting examples of the at least one additional ingredient include gelling agents, oils, waxes, preservatives, suspending agents, thickening agents, solvents, surfactants, emollients and other ingredients that, when incorporated into the inventive compositions, may stay on to the surface of the skin and may not strongly adhere to the skin.

Characteristics of the at least one additional ingredient may include the ability to impart an oily feeling and/or increased spreadability, for example, as observed with some esters and organic sunscreens. In one embodiment, where the inventive composition further comprises at least one additional ingredient, for example, to enhance the spreadability and the emollience of the product, the at least one additional ingredient is present in the composition in an amount that is sufficient to allow the composition to retain its transfer resistance and long wear properties.

Non-limiting examples of suspending agents and thickening agents suitable for use in the present invention as the at least one additional ingredient include waxes, silica gels, gums such as xanthan gum, cellulose derivatives, clays including organoclays, silicas such as fumed silica, fatty acid soaps, and various hydrocarbon gels. For example, hydrocarbon gels comprising di-block, tri-block, multi-block and/or radial or star block copolymers are used in the art as gelling agents, suspending agents, and/or dispersing agents. See e.g., U.S. Pat. No. 5,756,082, WO 98/42298, and EP 0497 144 B1, the disclosures of which are hereby incorporated by reference. Copolymers of this type are known in the art to have advantageous properties when used as suspension agents for various solids and liquids. See WO 98/38981, the disclosure of which is hereby incorporated by reference. In one embodiment, at least one thickening agent is present in the inventive composition in an amount generally ranging from 0.1% to 10% by weight relative to the total weight of the composition.

Non-limiting examples of emollients that may be used in the compositions of the present invention as the at least one additional ingredient include glycerine, propylene glycol, cyclomethicone, and dimethicone. Other non-limiting examples of suitable emollients include the compounds disclosed in the International Cosmetic Dictionary and Handbook Vol. 2, such as the emollients disclosed on pages 1656–1661, the disclosures of which are hereby incorporated by reference. In one embodiment, at least one emollient is present in the inventive composition in an amount ranging from 0.5% to 8% by weight relative to the total weight of the composition.

Other non-limiting examples of the at least one additional ingredient include fatty substances, waxes and formulation aids which are traditionally employed in the field of application envisaged. Non-limiting examples of fatty substances include silicones in esterified and unesterified liquid form and silicones in esterified solid form (such as behenate dimethicone), nonsilicone fatty substances (such as vegetable oils, mineral oils, animal oils, synthetic oils, vegetable pastes, mineral pastes, animal pastes, synthetic pastes, vegetable waxes, mineral waxes, animal waxes, and synthetic waxes). Non-limiting examples of suitable formulation aids include organic emulsifiers and organosilicone emulsifiers, such as, for example, those used in water-in-oil systems and those used in oil-in-water systems. Non-limiting examples of organic emulsifiers include any ethoxylated surfactants known in the art, such as Polysorbate-20, Laureth-7, and Laureth-4. Non-limiting examples of organosilicone emulsifiers include cetyl dimethicone copolyol-polyglyceryl-4-isostearate-hexylaurate (ABIL® WE 09) available from Goldschmidt Chemical Corporation, Cetyl Dimethicone Copolyol (ABIL® EM 90), (ABIL® EM 97), Laurylmethicone Copolyol (5200), Cyclomethicone (and) Dimethicone Copolyol (DC 5225 C) available from GE silicones, and Cyclopentasiloxane & Dimethicone Copolyol (GE SF 1528).

Formulation aids, if present, are present in the inventive compositions in an amount generally ranging from 1% to 15% by weight relative to the total weight of the composition. Further, these formulation aids may be selected by the person skilled in the art in order to prepare a composition which has the desired properties, such as, for example, consistency or texture. For example, the compositions according to the invention may include at least one of the above mentioned waxes, so as to ensure a good mechanical strength, such as, for example, when the composition is in the form of a stick.

Another non-limiting example of the at least one additional ingredient suitable for use in the inventive compositions is spherical compounds such as polyurethanes such as BPD 500, nylon 12, silica, acrylates, esters of acrylates, methacrylates such as polymethyl methacrylates, esters of methacrylates, and other microspheres. These spherical compounds, when present in the inventive compositions, may impart a smooth feeling when the composition is applied and spread onto skin.

Further, the at least one additional ingredient may be chosen from customary additives from the field of compositions to be applied in any cosmetic formulation (including cosmetic foundations, eyeliners, lip compositions, mascaras, eyeshadows, concealers, lotions) and any other aforementioned applications of the invention such as: hectorites; synthetic polymers (such as acrylic polymers or associative polymers of the polyurethane type); spreading agents; dispersants; antifoaming agents; wetting agents; UV-screening agents; antioxidants; perfumes; essential oils; essential fatty acids; pigments; mothers-of-pearl; fillers; cosmetic active agents; dermatological active agents; pharmaceutical active agents; moisturizers; vitamins; biological materials; and derivatives of any of the foregoing.

Non-limiting examples of pigments that may be used in the practice of the invention include titanium dioxide, D & C Red No. 7 Calcium Lake, D & C Red No. 21 Aluminum Lake, Iron Oxides, FD & C Yellow No. 5 Aluminum Lake, FD & C Blue No. 1 Aluminum Lake and any other pigments (including treated pigments) known in the cosmetic arts.

The at least one additional ingredient may be chosen from fillers and mothers-of-pearl. These ingredients may modify the texture of the inventive composition and the matteness/gloss effect. Non-limiting examples of pearling agents that may be used in the practice of the invention include mica, iron oxides, titanium dioxide and any other pearling agent known in the cosmetic arts.

Needless to say, a person skilled in the art will take care to select the at least one suitable additive such that the advantageous properties of the composition in accordance with the invention are not, or are not substantially, adversely affected by the addition(s) envisaged.

According to the present invention, the inventive compositions may enable the processing of a formulation and/or a product which comprises a large amount of a volatile solvent at a low temperature. In one embodiment, a formulation comprising at least one inventive composition is capable of being processed at a temperature of 55° C. or lower.

Further, the compositions of the present invention may provide at least one property chosen from long wear and transfer resistance in a broad range of applications. These applications include, for example, pigmented cosmetics (including foundations, concealers, mascaras, eyeliners, lipsticks, eyeshadows); hair compositions (including hair sprays, gels and mousses); sunscreen compositions; skin care and/or treatment compositions (including lotions, such as moisturizing lotions, lotions with active ingredients, and lotions with fragrances). The products of the present invention may be useful in any cosmetic, dermatological and/or pharmaceutical application which relates to formation of a flexible film that adheres strongly to the substrate to which it is applied.

As previously mentioned, the compositions of the present invention may also be effective in waterproofing. For example, the inventive compositions may retard dehydration of the substrate to which they are applied, such as skin, for example, by forming an occlusive film and reducing transepidermal water loss.

In one embodiment, the inventive compositions provide a barrier between the substrate and the environment, entrapping therein any active and/or functional ingredients. This barrier may boost the activity of any active and/or functional ingredients (such as, for example, the SPF and UV light protection of sunscreen ingredients) and may block the effect of humidity and the environment.

The present invention is also directed to cosmetic foundation compositions. In one embodiment, the foundation composition comprises (i) at least one polymethylsilsesquioxane film former, (ii) at least one film former different from the at least one polymethylsilsesquioxane film former, (iii) at least one thickening agent in an amount ranging from 0.1 to 10% by weight relative to the total weight of the composition, and (iv) at least one emollient in an amount ranging from 0.5% to 8% by weight relative to the total weight of the composition.

The present invention is also directed to a mascara composition. Mascara compositions comprising at least one polymethylsilsesquioxane film former, and at least one film former different from the at least one polymethylsilsesquioxane film former may, in one embodiment, provide at least one property chosen from long wear and transfer resistance. Further, the inventive mascara composition may provide waterproof properties.

In one embodiment, the inventive mascara composition comprises Resin MK (the at least one polymethylsilsesquioxane film former) and Versagel M5960 (the at least one film former different from the at least one polymethylsilsesquioxane film former). In another embodiment, the inventive mascara composition further comprises at least one allyl stearate/vinyl acetate copolymer film former. A non-limiting example of at least one allyl stearate/vinyl acetate copolymer film former is Mexomere® film former, and this copolymer film former may be present, for example, in an amount ranging from 0.5% to 10% by weight relative to the total weight of the composition.

Another subject of the present invention is compositions, such as, for example, suntan lotions and sunscreen lotions, comprising (i) at least one polymethylsilsesquioxane film former, (ii) at least one film former different from the at least one polymethylsilsesquioxane film former, and (iii) at least one UV absorber. These inventive compositions may provide at least one property chosen from long wear, transfer resistance, and waterproof properties.

Another subject of the present invention is eyeliner compositions. The inventive eyeliner compositions may provide at least one property chosen from long wear and transfer resistance. Further, the inventive eyeliner compositions may provide waterproof properties. In one embodiment, the eyeliner composition comprises Resin MK (the at least one polymethylsilsesquioxane film former) and at least one film former different from the at least one polymethylsilsesquioxane film former, such as Versagel M5970. In another embodiment, the inventive eyeliner composition further comprises at least one allyl stearate/vinyl acetate copolymer film former, such as a Mexomere® film former. The at least one allyl stearate/vinyl acetate copolymer film former may be present in the composition in an amount generally ranging from 0.5% to 3.5% by weight relative to the total weight of the composition.

According to the present invention, the inventive eyeliner compositions may further comprise at least one entity chosen from hydrocarbon gels, bentone type gels, waxes (such as beeswax, carnauba wax and derivatives thereof, preservatives, propylene carbonate, isododecane, silica, silica silylate, petroleum distillates, polyethylene, preservatives, and pigments (such as iron oxides, ultramarines, and black oxides). Non-limitiing examples of bentone type gels include Gel SS71, Gel EA2786, Quaternium-18 Bentonite, 38 CE, Gel ISD V and Gel ISD. For example, if present, bentone type gels may be present in the composition in an amount generally ranging from 0.5% to 50% by weight relative to the total weight of the composition.

The present invention is also directed to a make-up composition for lips, such as human lips, comprising the at least one polymethylsilsesquioxane, such as Resin MK, and at least one filmer former, such as Versagel M5970, in a quantity sufficient to obtain a transfer resistant film. The film may have at least one property chosen from long wear and transfer resistance.

The packaging and application device for any subject of the invention may be chosen and manufactured by persons skilled in the art on the basis of their general knowledge, and adapted according to the nature of the composition to be packaged. Indeed, the type of device to be used may be in particular linked to the consistency of the composition, such as to its viscosity; and may depend on the nature of the constituents present in the composition, such as the presence of volatile compounds.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. The following examples are intended to illustrate the invention without limiting the scope as a result.

EXAMPLE 1

An inventive mascara composition comprising at least one polymethylsilsesquioxane and at least one film former different from the polymethylsilsesquioxane was prepared. The wear and transfer characteristics of the inventive mascara were compared to a comparative mascara composition comprising trimethylsiloxysilicate instead of polymethylsilsesquioxane. All ingredients are listed in weight %.

|  | Composition A (Inventive) | Composition B (Comparative) |
| --- | --- | --- |
| Volatile solvent | 39.89 | 39.89 |
| Polymethylsilsesquioxane[1] | 8.00 | — |
| Trimethylsiloxysilicate[2] | — | 8.00 |
| Film formers (Isododecane and hydrogenated styrene-butylene-ethylene-styrene copolymer and hydrogenated ethylene-propylene-styrene copolymer[3]) | 16.50 | 16.50 |
| Bentone | 5.50 | 5.50 |
| Pigments | 6.00 | 6.00 |
| Emulsifier | 0.50 | 0.50 |
| Propylene Carbonate | 1.80 | 1.80 |
| Film Former | 5.00 | 5.00 |
| Waxes | 16.80 | 16.80 |
| Preservatives | 0.01 | 0.01 |

[1]: Silicone Resin MK available from Wacker
[2]: Resin MQ available from Dow Corning
[3]: Versagel MD5970 available from Penreco The inventive mascara A exhibited long wear and non transfer characteristics as well as a better feel. Further, the film deposited on the lashes by the inventive mascara A was less brittle than that deposited by the comparative mascara B.

EXAMPLE 2

An inventive make-up composition for lips comprising at least one polymethylsilsesquioxane and at least one film former different from the polymethylsilsesquioxane was prepared. The adhesion of the inventive composition was compared to a comparative lip composition comprising trimethylsiloxysilicate instead of polymethylsilsesquioxane. All ingredients are listed in weight %.

|  | Composition A (Inventive) | Composition B (Comparative) |
| --- | --- | --- |
| Waxes | 24.50 | 24.50 |
| Polymethylsilsesquioxane[1] | 15.00 | — |
| Trimethylsiloxysilicate[2] | — | 15.00 |
| Volatile solvents | 25.00 | 25.00 |
| Ester emollients | 11.70 | 11.70 |
| Silicone emollients | 10.00 | 10.00 |
| PVP/Hexadecene Copolymer | 4.60 | 4.60 |
| Acrylates copolymers | 1.00 | 1.00 |
| Pigments | 1.30 | 1.30 |
| Fillers | 6.50 | 6.50 |
| Preservatives | 0.40 | 0.40 |

[1]: Silicone Resin MK available from Wacker
[2]: Resin MQ available from Dow Corning The inventive composition A provided better adhesion.

EXAMPLE 3

An foundation composition comprising at least one polymethylsilsesquioxane film former (Resin MK) and at least one film former different from the polymethylsilsesquioxane film former was prepared. The adhesion of the inventive composition was compared to a comparative foundation composition comprising trimethylsiloxysilicate instead of polymethylsilsesquioxane. All ingredients are listed in weight %.

|  | Composition A (Inventive) | Composition B (Comparative) |
| --- | --- | --- |
| Phase A |  |  |
| Organosilicone emulsifier | 8.00 | 8.00 |
| Ester emollient | 2.50 | 2.50 |
| Pigments | 10.00 | 10.00 |
| Fillers | 1.00 | 1.00 |
| Preservative | 0.10 | 0.10 |
| Phase B |  |  |
| Volatile Solvent | 15.00 | 15.00 |
| Bentone | 0.80 | 0.80 |
| Propylene carbonate | 0.15 | 0.15 |
| Trimethylsiloxysilicate resin[1] | — | 12.00 |
| Resin MK[2] | 12.00 | — |
| Film formers (Isododecane & hydrogenated styrene-butylene-ethylene-styrene copolymer and hydrogenated ethylene-propylene-styrene copolymer[3]) | 8.00 | 8.00 |
| Phase C |  |  |
| Propylene Glycol | 1.50 | 1.50 |
| Preservative | 0.40 | 0.40 |
| Phase D | 1.45 | 1.45 |
| Fillers |  |  |
| Phase E |  |  |
| Distilled Water | 38.00 | 38.00 |
| Emulsifier | 0.20 | 0.20 |
| Preservative | 0.30 | 0.30 |
| Salt | 0.60 | 0.60 |

[1]: Trimethylsiloxysilicate resin available from GE as SR1000
[2]: Silicone Resin MK available from Wacker
[3]: Versagel MD570 from Penreco.

The inventive composition had more slip upon application, i.e., was easier to apply, and provided more coverage.

What is claimed is:

1. A composition comprising
   (a) at least one polymethylsilsesquioxane film former comprising repeating units of formula $(CH_3SiO_{3/2})$ and
   (b) at least two film formers different from said at least one polymethylsilsesquioxane film former,
   wherein said composition is a mascara composition;
   further wherein x is the number of repeating units; and
   further wherein said at least one polymethylsilsesquioxane film former is present in an amount effective to provide at least one property chosen from long wear and transfer resistance,
   wherein at least one of said at least two film formers in (b) is chosen from allyl stearate/vinyl acetate copolymer film formers.

2. The composition according to claim 1, wherein said at least one polymethylsilsesquioxane film former is present in an amount effective to provide long wear and transfer resistant properties.

3. The composition according to claim 1, wherein x is less than or equal to 500.

4. The composition according to claim 1, wherein x ranges from 50 to 500.

5. The composition according to claim 1, wherein said at least one polymethylsilsesquioxane film former has a melting point ranging from 40° C. to 80° C.

6. The composition according to claim 1, wherein said at least one polymethylsilsesquioxane film former further comprises up to 1% of units of formula $(CH_3)_2SiO_{3/2}$.

7. The composition according to claim 1, wherein said at least one polymethylsilsesquioxane film former has a weight average molecular weight ranging from 500 to 20,000.

8. The composition according to claim 7, wherein said at least one polymethylsilsesquioxane film former has a weight average molecular weight of 10,000.

9. The composition according to claim 1, wherein said at least one polymethylsilsesquioxane film former is present in an amount ranging from 1% to 25% by weight relative to the total weight of the composition.

10. The composition according to claim 9, wherein said at least one polymethylsilsesquioxane film former is present in an amount ranging from 5% to 20% by weight relative to the total weight of the composition.

11. The composition according to claim 1, wherein said at least one polymethylsilsesquioxane film former is present in said composition in a higher amount than the amount of said at least one film former different from said at least one polymethylsilsesquioxane film former.

12. The composition according to claim 1, wherein said at least two film formers different from said at least one polymethylsilsesquioxane film former are chosen from di-block copolymer film formers, tri-block copolymer film formers, multi-block copolymer film formers, radial block copolymer film formers, and star block copolymer film formers.

13. The composition according to claim 1, wherein said at least two film formers different from said at least one polymethylsilsesquioxane film former are chosen from:
styrene-butadiene-styrene block copolymers;
styrene-isoprene-styrene block copolymers;
styrene-ethylenebutylene-styrene block copolymers;
styrene-ethylenepropylene block copolymers;
styrene-ethylenebutylene block copolymers;
styrene-butadiene block copolymers;
styrene-isoprene block copolymers;
styrene-butylene-ethylene-styrene block copolymers; and
ethylene-propylene-styrene block copolymers.

14. The composition according to claim 1, wherein said at least two film formers different from the at least one polymethylsilsesquioxane film former are present in an amount ranging from 1% to 25% by weight relative to the total weight of the composition.

15. The composition according to claim 1, further comprising at least one additional ingredient chosen from gelling agents; oils; waxes; preservatives; suspending agents; thickening agents; solvents; surfactants; emollients; fatty substances; waxes; formulation aids; spherical compounds; hectorites; synthetic polymers; spreading agents; dispersants; antifoaming agents; wetting agents; UV-screening agents; antioxidants; perfumes; essential oils; essential fatty acids; pigments; mothers-of-pearl; fillers; cosmetic active agents; dermatological active agents; pharmaceutical active agents; moisturizers; vitamins; biological materials; and derivatives of any of the foregoing, wherein said at least one additional ingredient is different from both the at least one polymethylsilsesquioxane film former and the at least one film former different from the at least one polymethylsilsesquioxane film former.

16. The composition according to claim 1, wherein said allyl stearate/vinyl acetate copolymer film former is present in an amount ranging from 0.5% to 10% by weight relative to the total weight of the composition.

17. The composition according to claim 16, wherein said composition is waterproof.

18. A composition comprising:
(a) at least one polymethylsilsesquioxane film former comprising repeating units of formula $(CH_3SiO_{3/2})$ and
(b) at least two film formers different from said at least one polymethylsilsesquioxane film former,
wherein said composition is an eyeliner composition;
further wherein x is the number of repeating units; and
further wherein said at least one polymethylsilsesquioxane film former is present in an amount effective to provide at least one property chosen from long wear and transfer resistance,
wherein at least one of said at least two film formers in (b) is chosen from allyl stearate/vinyl acetate copolymer film formers.

19. The composition according to claim 18, wherein x is less than or equal to 500.

20. The composition according to claim 18, wherein x ranges from 50 to 500.

21. The composition according to claim 18, wherein said at least one polymethylsilsesquioxane film former has a melting point ranging from 40° C. to 80° C.

22. The composition according to claim 18, wherein said at least one polymethylsilsesquioxane film former further comprises up to 1% of units of formula $(CH_3)_2SiO_{3/2}$.

23. The composition according to claim 18, wherein said at least one polymethylsilsesquioxane film former has a weight average molecular weight ranging from 500 to 20,000.

24. The composition according to claim 23, wherein said at least one polymethylsilsesquioxane film former has a weight average molecular weight of 10,000.

25. The composition according to claim 18, wherein said at least one polymethylsilsesquioxane film former is present in an amount ranging from 5% to 70% by weight relative to the total weight of the composition.

26. The composition according to claim 25, wherein said at least one polymethylsilsesquioxane film former is present in an amount ranging from 20% to 70% by weight relative to the total weight of the composition.

27. The composition according to claim 18, wherein said at least one polymethylsilsesquioxane film former is present in said composition in a higher amount than the amount of said at least one film former different from said at least one polymethylsilsesquioxane film former.

28. The composition according to claim 18, wherein said at least two film formers different from said at least one polymethylsilsesquioxane film former are chosen from di-block copolymer film formers, tri-block copolymer film formers, multi-block copolymer film formers, radial block copolymer film formers, and star block copolymer film formers.

29. The composition according to claim 18, wherein said at least two film formers different from said at least one polymethylsilsesquioxane film former are chosen from:
styrene-butadiene-styrene block copolymers;
styrene-isoprene-styrene block copolymers;
styrene-ethylenebutylene-styrene block copolymers;
styrene-ethylenepropylene block copolymers;
styrene-ethylenebutylene block copolymers;
styrene-butadiene block copolymers;
styrene-isoprene block copolymers;
styrene-butylene-ethylene-styrene block copolymers; and
ethylene-propylene-styrene block copolymers.

30. The composition according to claim 18, wherein said at least two film formers different from the at least one polymethylsilsesquioxane film former are present in an amount ranging from 1% to 25% by weight relative to the total weight of the composition.

31. The composition according to claim 18, further comprising at least one additional ingredient chosen from gelling agents; oils; waxes; preservatives; suspending agents; thickening agents; solvents; surfactants; emollients; fatty substances; waxes; formulation aids; spherical compounds; hectorites; synthetic polymers; spreading agents; dispersants; antifoaming agents; wetting agents; UV-screening agents; antioxidants; perfumes; essential oils; essential fatty acids; pigments; mothers-of-pearl; fillers; cosmetic active agents; dermatological active agents; pharmaceutical active agents; moisturizers; vitamins; biological materials; and derivatives of any of the foregoing, wherein said at least one additional ingredient is different from both the at least one polymethylsilsesquioxane film former and the at least one film former different from the at least one polymethylsilsesquioxane film former.

32. The composition according to claim 31, further comprising at least one additional ingredient chosen from hydrocarbon gels, bentone type gels, waxes, preservatives, propylene carbonate, isododecane, silica, silica silylate, petroleum distillates, polyethylene, preservatives, and pigments.

33. The composition according to claim 18, wherein said allyl stearate/vinyl acetate copolymer film former is present in an amount ranging from 0.5% to 3.5% by weight relative to the total weight of the composition.

* * * * *

UNITED STATES PATENT AND TRADEMARK OFFICE
CERTIFICATE OF CORRECTION

PATENT NO. : 6,991,782 B2  
APPLICATION NO. : 09/883229  
DATED : January 31, 2006  
INVENTOR(S) : Mohamed Kanji et al.

Page 1 of 1

It is certified that error appears in the above-identified patent and that said Letters Patent is hereby corrected as shown below:

In claim 1, column 16, line 17, "$(CH_3SiO_{3/2})$ and" should read --$(CH_3SiO_{3/2})_x$; and--.

In claim 18, column 17, line 40, "$(CH_3SiO_{3/2})$ and" should read --$(CH_3SiO_{3/2})_x$; and--.

Signed and Sealed this

Twenty-second Day of September, 2009

David J. Kappos  
*Director of the United States Patent and Trademark Office*